United States Patent [19]
Phan et al.

[11] Patent Number: 5,424,303
[45] Date of Patent: Jun. 13, 1995

[54] SUBSTITUTED AMINOPHOSPHONATE DERIVATIVES, PROCESS FOR THEIR PREPARATION AND PHARMACEUTICAL COMPOSITIONS CONTAINING THEM

[75] Inventors: Hieu T. Phan, Tannay; Lân M. Nguyen; Eric Niesor, both of Nyon, all of Switzerland; Yves Guyon-Gellin, Annemasse, France; Craig L. Bentzen, Bogis-Bossey, Switzerland

[73] Assignee: Symphar SA, Versoix, Switzerland

[21] Appl. No.: 24,731

[22] Filed: Feb. 26, 1993

[30] Foreign Application Priority Data

Mar. 5, 1992 [CH] Switzerland .................. 704/92

[51] Int. Cl.$^6$ .................. C07F 9/58; C07F 9/28; A61K 31/675
[52] U.S. Cl. .................. 514/89; 546/22; 546/24; 548/113; 548/115; 548/413; 549/220; 549/221; 558/166; 558/168; 558/169; 558/190
[58] Field of Search .................. 546/22, 24; 514/89

[56] References Cited

PUBLICATIONS

Chemical Abstracts 1, vol. 84(9), 84:59666j, Mar. 1, 1976.
Chemical Abstracts II, vol. 85(15), 85:108717h, Oct. 11, 1976.
Chemical Abstracts III, vol. 107, (11), 111:96790j, Sep. 14, 1987.
"High Density Lipoprotein As a Protective Factor Against Coronary Heart Disease", The American Journal of Medicine, vol. 62, T. Gordon et al., pp. 707–717, May 1977.
"The influence of changes in lipid values induced by cholestryamine and diet on progression of coronary artery disease": results of the NHLBI Type 11 Coronary Intervention Study, (Feb. 1984) vol. 69, No. 2, 1984, By R. Levy et al., pp. 325–337.
"Helsinki Health Study: Primary Prevention Trial with Gemfibrozil in Middle–Ages Men with Dyslipidemia", The New England Journal of Medicine, vol. 317, No. 20, Nov. 1987, By M. Frick et al.
"Beneficial Effects of Combined Colestipol–Niacin Therapy on coronary Atherosclerosis and Coronary Venous Bypass Grafts", Journal of American Medicine, vol. 257, No. 23, Jun. 1987, By D. Blacnkenhorn et al., pp. 3233–3240.
Metabolism of Lipoproteins and Their Role in the Pathogenesis of "Atherosclerosis", Atherosclerosis Reviews, vol. 18, 1988, By D. Steinberg, pp. 1–23.
"Antiatherogenic effect of probucol unrelated to its hypocholesterolemic . . . ", vol. 84, Nov. 1987, Medical Sciences, By T. Carew et al. pp. 7725–7729.
"Probucol prevents the progression of atherosclerosis in Watanabe Heritable . . . ", Medical Sciences, vol. 84, Aug. 1987, By T. Kita et al., pp. 5928–5931.

(List continued on next page.)

Primary Examiner—Alan L. Rotman
Attorney, Agent, or Firm—Young & Thompson

[57] ABSTRACT

The present invention relates to novel aminophosphonate derivatives substituted in α position by phenol groups, of formula (I):

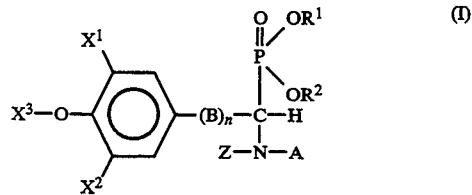

in which:
$X^1$, $X^2$, $X^3$, $R^1$, $R^2$, A, B, Z and n are defined in claim 1, as well as their preparations and the pharmaceutical compositions comprising them.

5 Claims, No Drawings

SUBSTITUTED AMINOPHOSPHONATE DERIVATIVES, PROCESS FOR THEIR PREPARATION AND PHARMACEUTICAL COMPOSITIONS CONTAINING THEM

This invention relates to a novel class of compounds, aminophosphonates substituted at alpha position by phenol groups as well as the processes for their preparation. The invention further relates to the pharmaceutical compositions containing the above mentioned compounds, especially for the treatment of hyperlipidemia and hypercholesterolemia which are at the origin of the arteriosclerotic process.

Plasma cholesterol, in particular cholesterol transported by low density lipoproteins (LDL), is a key factor in the pathology of cardiovascular diseases (T. Gordon et al, The Framingham Study, *Am. I. Med.* 62, 707, 1977). It has been shown recently that the use of hypocholesterolemic drugs could decrease the incidence of cardiovascular diseases (R. Z. Levy et at, Results of the NHLBP Type II Coronary Intervention Study, *Circulation* 69, 325, 1984; M. H. Frick et at, The Helsinki Heart Study, *N. Engl. J. Med.*, 317, 1237-1245, 1987).

The studies of D. H. Blankenhom et al (*J. Am. Med. Ass.* 2.57, 3233-3240, 1987; *J. Am. Med. Ass.* 259, 2698, 1988) have clearly demonstrated that it was possible to prevent the progression or furthermore, to facilitate the regression of the already formed atherosclerotic coronary plaques by a therapeutic approach. The studies of Steinberg's group (Atherosclerosis Reviews Vol. 18, 1-23, 1988) have shown that the oxidation of low density lipoproteins is at the origin of the formation of foam cells which contribute to deposition of cholesterol in the arteries (atherosclerotic plaques) or in tendons and skin (xanthomas).

The hypocholesterolemic and antioxidant drug Probucol prevents the deposition of cholesterol in the arteries of hereditary atherosclerotic robbits (T. E. Carew et at, *Proc. Natl. Acad. Sci. USA* 84, 7725-7729, 1987; T. Kita et at, *Proc. Natl. Acad. Sci. USA* 84, 5928-5931, 1987) and induces the regression of xanthomas in patients suffering from familial hypercholesterolemia (A. Yamamoto et at, *Am. J. Cardioh* 57, 29-35, 1986). These results are proof that it is possible to decrease or to prevent the deposition of arterial or peripheric tissue cholesterol by using potent hypocholesterolemic and antioxidant drugs, these two properties being synergistic.

On the other hand, a survey of the literature has shown that known amino-phosphonic acids, which are analogs of amino acids, possess a large spectrum of biological and pharmacological properties and are enzyme inhibitors, antimicrobial agents, herbicidal agents, anticancer agents, antiosteoclastic agents (K. Issleib, Phospha-Pharmaka, *Nachr. Chem. Tech. Lab.* 35 (10), 10:37-1042, 1977). The present inventors have found useful to incorporate to the aminophosphonate function a phenol substituent derived from the BHT compound (2,6-di-tert-butyl-4-methyl phenol).

The experiments performed by the present inventors have shown that some aminophosphonates, in particular those substituted at the alpha position by phenol groups, are potent hypocholesterolemic compounds and furthermore, have remarkable antioxidant properties. Therefore, these aminophosphonates are potentially drugs of choice for treating cardiovascular and metabolic diseases induced by or associated with lipid (cholesterol) metabolism perturbation or with a decrease of defense mechanisms due to "oxidative stress".

The aminophosphonate derivatives, which present the above mentioned properties and which are described by the present invention are compounds of general formula (I)

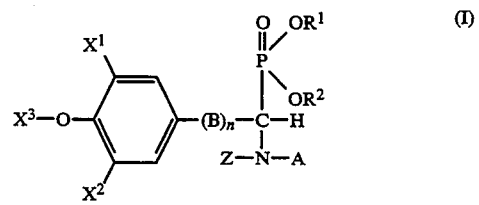

where:

$X^1$, $X^2$, identical or different, are H, a straight or branched alkyl or alkoxy group having from 1 to 8 carbon atoms, a hydroxy group or a nitro group, $X^3$ is H, an alkyl group from 1 to 4 carbon atoms, $X^3O$ and one of the two other substituents $X^1$ or $X^2$ may form an alkylidene dioxy ring having from 1 to 4 carbon atoms, $R^1$, $R^2$, identical or different, are H, a straight or branched alkyl group having from 1 to 6 carbon atoms, B is $CH_2$, $CH_2$—$CH_2$ or $CH=CH$, n is zero or 1, Z is H, a straight or branched alkyl group having from 1 to 8 carbon atoms, an acyl group $R^3$—CO where $R^3$ is an alkyl group from 1 to 4 carbon atoms, a perfluoroalkyl group from 1 to 4 carbon atoms.

A is H, $CH_2$—$CH=CH_2$, a straight, branched or cyclic alkyl group having from 1 to 8 carbon atoms, or is selected from the following groups:

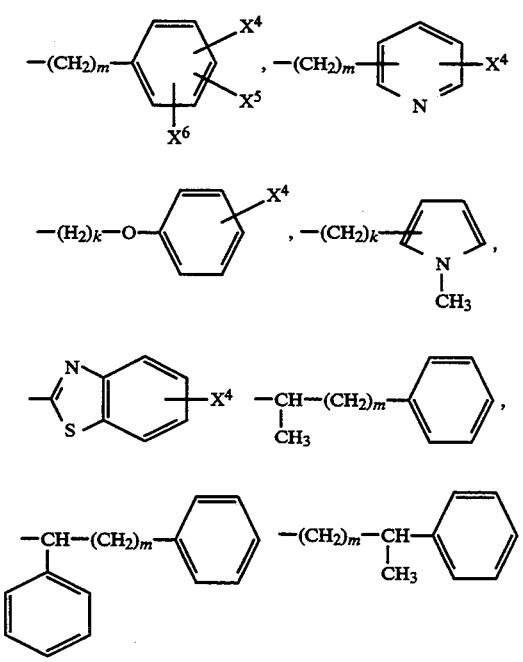

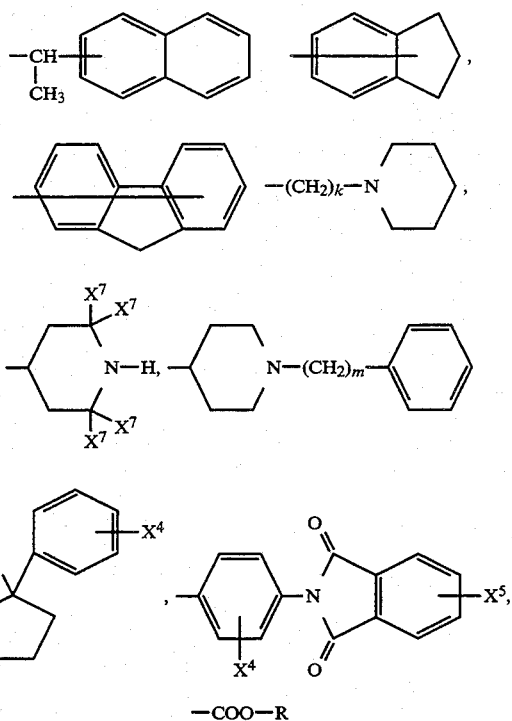

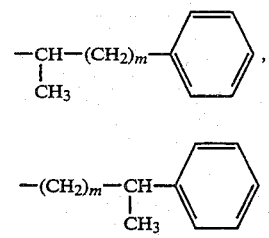

where:
k is an integer from 2 to 4, m is an integer from 0 to 5, $X^4$, $X^5$, $X^6$, identical or different, are H, a straight or branched alkyl or alkoxy group from 1 to 8 carbon atoms, a hydroxy, trifluoromethyl, nitro, amino, dimethylamino, diethylamino group, a halogen atom (F, Cl, Br, I), $X^4$ and $X^5$ may form an alkylidendioxy ring having from 1 to 4 carbon atoms, $X^7$ is H or $CH_3$, R is a straight or branched alkyl group having from 1 to 6 carbon atoms, an aryl or alkylaryl group from 6 to 9 carbon atoms.

According to the specific examples of the invention, the compounds of formula (I) include those in which:

$X^3$ is H or an alkyl group having from 1 to 4 carbon atoms, preferably $X^3$ is H, $X^1$ and $X^2$, identical or different, are a straight or branched alkyl group having from 1 to 6 carbon atoms, preferably $X^1$ and $X^2$ are both t-butyl, $R^1$ and $R^2$ are each H or a straight or branched alkyl group from 1 to 4 carbon atoms, preferably Ethyl, B is $CH_2$, n is zero or 1, preferably n is zero, Z is H, a straight or branched alkyl group from 1 to 4 carbon atoms, an acyl group $R^3$—CO— where $R^3$ is a $C_{1-4}$ alkyl group, and, A is H or is selected from the following groups:

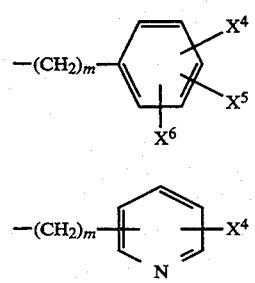

where m, $X^4$, $X^5$, $X^6$ are as previously defined.

This invention also relates to the processes for the preparation of compounds of formula (I), represented in page 9.

Following procedure a), aminophosphonates of formula (I) are prepared by nucleophilic addition of a phosphite on the imine (IV) obtained by condensation of the aldehyde (II) with the primary amine (III). The appropriate aldehyde and amine are reacted with or without a catalyst in a solvent such as ether, tetrahydrofuran, benzene, toluene or ethanol. The catalyst can be a molecular sieve, an acid such as glacial acetic acid, p-toluenesulfonic acid, thionyl chloride, titanium tetrachloride, boron trifluoride etherate, or a base such as potassium carbonate. The reaction is carried out at temperatures between 0° and the boiling point of the solvent used. Reaction times vary between one hour to one day. For the less reactive aldehydeamine series, condensation can be brought about by azeotropic distillation with benzene or toluene as solvent in a Dean-Stark apparatus.

Some imine derivatives (IV) can be isolated, purified, characterized and possibly tested for their biological properties. In general, however, they are used directly in the next reaction step.

The nucleophilic addition of a phosphite on the carbon atom of an imine can be carried out by reacting the relevant reactants imine (IV) and dialkyl phosphite (V) or its derivative trimethylsilyl-dialkyl phosphite $(Me_3SiO)P(OR^1)OR^2$ (VI) with or without using as catalyst an amine, such as diethyl amine or triethyl amine. In addition, the addition can be carried out by using the salt of dialkyl phosphite formed in situ by reacting dialkyl phosphite with a base such as sodium hydride, sodium methoxide or ethoxide. The reaction is carried out with or without a solvent such as petroleum ether, benzene, toluene, diethyl ether, tetrahydrofuran, 1,2-dimethoxyethane at a temperature between 30° and 140° C. Reaction times vary between 2 h and overnight.

In the case of secondary amines, the corresponding aminophosphonate (I) is prepared by reacting aldehyde (II) with equimolar amounts of the secondary amine (III) and dialkyl phosphite (V) dissolved in a hydrocarbon solvent such as petroleum ether, benzene, toluene, xylene at a temperature between room temperature and the boiling point of the selected solvent. The reaction can last between 15 min and several days.

According to procedure b), the aminophosphonates of formula (I) where A and Z are both hydrogen atoms, are easily prepared by catalytic hydrogenation of the corresponding amino phosphonate of formula (I) where Z is hydrogen and A an alpha substituted benzyl group such as 1-phenyl ethyl, 1-phenyl cyclopentyl or a benzyloxycarbonyl group. The catalyst can be palladium on charcoal or palladium (II) hydroxide on charcoal, the solvent can be ethanol or glacial acetic acid.

The aminophosphonic acids of formula (I) can be obtained by nucleophilic addition of phosphorous acid (V) on the appropriate imine (IV). The reaction is carried out with or without a solvent (benzene, toluene) at a temperature between 80° and 140° C. The aminophosphonic acids of formula (I) can also be prepared by hydrolysis of their corresponding esters according to established literature methods by using reagents such as hydrochloric acid, hydrobromic acid, bromotrimethyl silane or iodotrimethyl silane.

According to procedure c), the N-acylated aminophosphonates of formula (I) where $Z=R^3$—CO are obtained by acylation of the corresponding aminophosphonates (I) where $Z=H$, the acylating agent can be $R^3$—CO—Cl or $(R^3CO)_2O$ (VII). The reaction is carried out in a solvent such as petroleum ether, benzene, toluene, ether, tetrahydrofuran, with a tertiary base such as triethylamine.

When $R^1$, $R^2$ are hydrogen, the aminophosphonic acids (I) can form salts with inorganic or organic bases. These inorganic salts can be ammonium salts, salts of alkali or alkalino-earth metals such as lithium, sodium, potassium, magnesium or calcium. The organic salts can be salts of amines such as alkylamines, e.g. triethylamine, dicyclohexylamine, alkanolamines, e.g. diethanolamine, benzylamines, e.g. dibenzylamine, heterocyclic amines, e.g. morpholine etc. . . . These salts are integral part of the invention.

Through their amino function, the aminophosphonate esters (I) can form salts of inorganic acids such as HCl, $H_2SO_4$ or with organic acids such as oxalic acid, maleic acid, etc . . . An example of hydrochloride salt of aminophosphonate (I) is provided (example 2). All these salts are integral part of this invention.

Compounds of structure (I) have at least one asymmetrical center which is the carbon atom in position alpha to the phosphonate group. The compounds (I) therefore exist under the two enantiomeric forms. The racemic mixtures (50% of each enantiomer) and the pure enantiomers are comprised in the scope of this application.

The structures of compounds of formula (I) are established by their elemental analysis, their infrared (IR), mass (MS) and nuclear magnetic resonance (NMR) spectra. The purity of the compounds is checked by thin layer, gas liquid or high performance liquid chromatographies.

The abbreviations used in this application are the following: in the tables, n is normal, i is iso, s is secondary and t is tertiary. In the description of the NMR spectra, respectively s is singlet, d doublet, t triplet and m multiplet. The temperatures were recorded in Celsius degrees and the melting points are not corrected.

This invention is illustrated by the examples 1-23 which are representative of the compounds in the application and of the processes of synthesis employed.

SYNTHETIC PROCESSES

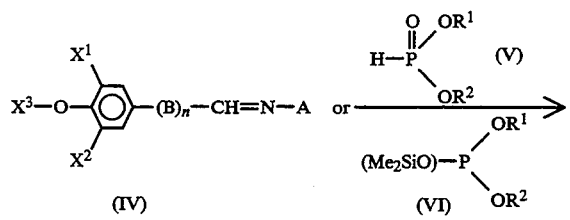

EXAMPLE 1 (compound 22)

Diethyl α-(3,5-di-tert-butyl-4-hydroxyphenyl)-N-(3-phenylpropyl)aminomethylphosphonate

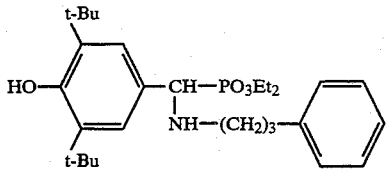

A solution containing 312.7 g ( 1.35 mol) of 3,5-di-tert-butyl-4-hydroxybenzaldehyde in 2400 ml THF was added to a solution of 189.4 g (1.40 mol) of 3-phenylpropyl-amine in 200 ml THF. The resulting mixture was stirred at room temperature for 24h. The solution was then dried with $MgSO_4$ and evaporated to dryness to yield 480 g of a light brown solid which was recrystallized in petroleum ether. 400 g of a yellow solid were obtained; mp=86°-87° C.; yield=86%. IR (KBr): 1610 cm$^{-1}$: CH=N.

To the previously obtained imine (350 g, 0.997 mol) dissolved in 220 ml toluene by slight warming was added dropwise diethyl phosphite (172 g, 1.25 mol). The resulting mixture was refluxed for 7 h then toluene was removed under vacuum. The viscous mass was triturated in hot petroleum ether and after cooling, was filtered and dried. Recrystallization in t-butyl methyl ether gave 340 g of a white solid, yield=66%, mp=99°-100° C. Elemental analysis $C_{28}H_{44}NO_4P$ % Calc. C 68.68 H 9.06 N 2.86 % Found C 68.45 H 9.36 N 2.74 IR (KBr): 3340 cm$^{-1}$: OH, 3240 (broad): NH, 1440: tert-Bu, 1190: P=O, 1120: P-OEt, 1030: P—O—C. MS: m/e=488: M$^+$−1,351: 488-$PO_3Et_2$ NMR ($CDCl_3$): δ=7.22 (m, 5H): phenyl H 7.20 (d, $J_{P-H}$ =2.2 Hz, 2H): aromatic H, 3,5-di-t-butyl-4-hydroxy phenyl 5.20 (s, 1H):OH 4.08, 3.95 and 3.80 (3 m, 4H): P—O—CH$_2$—CH$_3$ 3.94 (d, $J_{P-H}$=19 Hz, 1H): CH—$PO_3Et_2$ 2.65 (m, 4H): NH—CH$_2$—CH$_2$—CH$_2$—Ph 1.80 (m, 3H): NH—CH$_2$—CH$_2$—CH$_2$—Ph 1.45 (s,18H): tert-Bu 1.30 and 1.12 (2t, J=7 Hz, 6H): P—O—CH2—CH3

EXAMPLE 2 (compound 26)

Hydrochloride salt of diethyl α-(3,5-di-tert-butyl-4-hydroxyphenyl),N-(3-phenylpropyl)-animomethylphosphonate

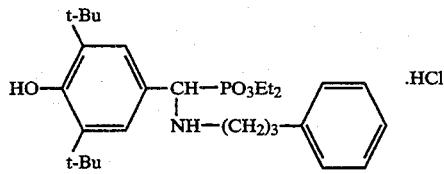

A solution of diethyl α-(3,5-di-tert-butyl-4-hydroxyphenyl)-N-(3-phenylpropyl) aminomethylphosphonate (3.0 g, 6.13 mmol) in 50 ml ether was cooled to −10° C. and was saturated with gazeous hydrogen chloride. The closed flask was left in the freezer overnight. Evaporation of the solvent gave 3.3 g of a solid which was recrystallized in ethanol/water.

mp=132°-134° C. with volume contraction IR (KBr): 3620 cm$^{-1}$: OH, 2700 (broad) +1600+1330: NH$_2$, 1230: P=O, 1160: P-O-Et, 1040: P—O—C. Elemental analysis $C_{28}H_{45}ClNO_4P$ % Calc. C 63.92 H 8.62 Cl 16.74 N 2.66 P 5.89 % Found C 63.57 H 8.46 Cl 16.52 N 2.56 P 5.71

EXAMPLE 3. (compound 17)

Diethyl α-(3,5-di-tert-butyl-4-hydroxyphenyl)-N-[2-(4-chlorophenyl)ethyl]-aminomethylphosphonate

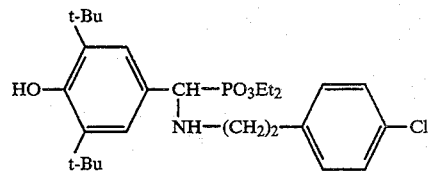

A mixture of 80.2 g (342 mmol) 3,5-di-tert-butyl-4-hydroxybenzaldehyde and 56.0 g (360 mmol) 2-(4-chlorophenyl)ethylamine dissolved in 750 ml THF was stirred at room temperature for 24 h. The solution was dried with $MgSO_4$, filtered and evaporated. The solid residue was recrystallized in ligroin to yield 101 g; 79% yield.

mp=116°-119° C. IR (KBr): 1610 cm$^{-1}$: CH=N

The above imine (9.0 g, 24.1 mmol) was dissolved in 57 ml toluene. Diethyl phosphite (4.2 g, 30.2 mmol) was added dropwise and the mixture was refluxed for 5 h. The solvent was evaporated to yield 14.0 g of solid residue. Recrystallization in 30 ml ligroin, then 30 ml t-butyl methyl ether gave 9.0 g (74% yield) of a solid, mp=119.5°-121° C. Elemental analysis $C_{27}H_{41}ClNO_4P$ % Calc. C 63.58 H 8.10 N 2.75 P 6.07 % Found C 63.77 H 8.30 N 2.80 P 6.21 IR(KBr): 3480 cm$^{-1}$: OH, 3400 (broad): NH, 1440: tert-Bu, 1230: P=O, 1100: Ph-Cl 1, 1030: P—O—C. NMR ($CDCl_3$): δ=7.23 and 7.10 (2d, J=8 Hz, 4H): aromatic H, 4-chlorophenyl 7.11 (d, $J_{P-H}$=2 Hz, 2H): aromatic H, 3,5-di-tert-butyl-4-hydroxyphenyl 5.20 (s, 1H): OH 4.00, 3.91 and 3.78 (3 m, 4H): P—O—CH$_2$CH$_3$ 3.94 (d, $J_{P-H}$=19 Hz, 1H): CH—$PO_3Et_2$ 2.80 (m, 2H): NH—CH$_2$—CH$_2$—Ph—Cl 2.75 (m, 2H): NH—CH$_2$—CH$_2$Ph—Cl 1.90 (broad): NH—1.44 (s, 18H): tert-Bu 1.25 and 1.10 (2t, J=7 Hz, 6H): P—O—CH$_2$—CH$_3$ MS: m/e=372:M$^+$−$PO_3Et_2$

EXAMPLE 4 (compound 42)

Diethyl α-(3,5-di-tert-butyl-4-hydroxyphenyl)-N-(3-picolyl)-aminomethylphosphonate

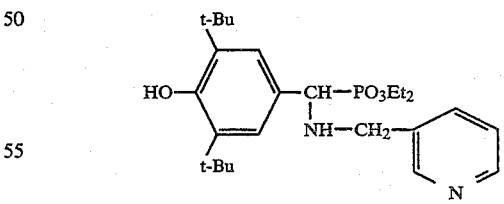

A mixture of 5.0 g (21.4 mmol) of 3,5-di-t-butyl-4-hydroxy benzaldehyde, 2.34 g (21.6 mmol) of 3-picolylamine and 6.0 g (42.8 mmol) anhydrous potassium carbonate in 50 ml benzene was refluxed for one day. The potassium carbonate was filtered and the solvent was evaporated. The residue was heated at 140° C. with 3.0 g (21.6 mmol) of diethylphosphite for 3 h. An amount of 6.6 g of compound was isolated by column chromatography (95/5 CHCl$_{13}$/MeOH), which gave 5.9 g (60%) after recrystallization in petroleum ether;

mp=100°-101° C. IR (film): 3650 cm⁻¹:OH, 3300 (large): NH, 1430: tert-Bu, 1230: P=O, 1030: P—O—C, NMR (CDCl₃): δ=8.50, 7.65 and 7.25 (3 m, 4H): aromatic H, 3-picolyl 7.20 (d, J$_{P-H}$=2 Hz, 2H): aromatic H, 3,5-di-butyl-4-hydroxyphenyl 5.25 (s, 1H): OH 4.08, 3.94 and 3.80 (3m, 4H): P—O—CH₂CH₃ 3.91 (d, J$_{P-H}$=19 Hz, 1H): CH—PO₃Et₂ 3.81 and 3.61 (2d, J=13 Hz, 2H): NH—CH₂—Py 2.20 (broad): NH-, 1.45 (s, 18H): tert-Bu 1.30 and 1.10 (2t, J=7 Hz, 6H): P—O—CH2CH₃ MS: m/e=462: M+, 324:M+—H—PO₃Et₂(base peak) Elemental analysis C₂₅H₃₉N₂O₄P % Calc C 64.91 H 8.50 N 6.06 P 6.70 % Found C 64.83 H 8.70 N 5.88 P 6.45

EXAMPLE 5 (compound 44)

Diethyl α-(3.5-di-tert-butyl-4-hydroxyphenyl)-N-(2-benzothiazolyl)-aminomethylphosphonate

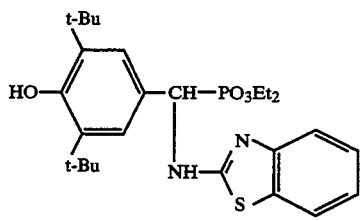

A solution of 5.0 g (21.4 mmol) 3,5-di-tert-butyl-4-hydroxybenzaldehyde and 3.2 g (21.6 mmol) 2-aminobenzothiazole dissolved in 60 ml toluene: contained in a flask connected to a Dean-Stark apparatus was heated to reflux overnight. Toluene was evaporated under vacuum then the residue was heated with 3.0 g (21.6 mmol) diethyl phosphite at 140° C. for 3 h. The title compound was purified by column chromatography with a mixture of 95/5 CHCl₃/MeOH. Trituration in petroleum ether gave 6.5 g (60% yield) of a solid; mp=198°-199° C. IR(KBr): 3620 cm⁻¹: OH, 3260: NH, 1540: C=N, benzothiazole, 1450: tert-Bu, 1240: P=O, 1030: P—O—C. NMR(CDCl₃) δ=7.56, 7.29 and 7.09 (3 m, 4H): aromatic H, benzothiazolyl 7.33 (d, J$_{P-H}$=2 Hz, 2H): aromatic H, 3,5-di-t-butyl-4-hydroxyphenyl 6.55 (broad): NH—5.32 (d, J$_{P-H}$=21.5 Hz, 1H): CH—PO₃Et₂ 5.25 (s, 1H): OH 4.17, 3.98 and 3.75 (3m, 4H): P—O—CH₂—CH₃ 1.45 (s, 18H): tert-Bu 1.28 and 1.08 (2t, J=7 Hz, 6H): P—O—CH₂—CH₃ MS: m/e=504: M+, 367: M+—PO₃Et₂ (base peak)

EXAMPLE 6 (compound 49)

Diethyl α-(3.,5-di-tert-butyl-4-hydroxyphenyl)-N-methyl-N-(3-picolyl) aminomethylphosphonate

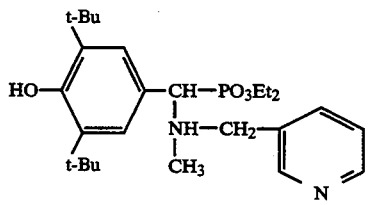

3,5-Di-tert-butyl-4-hydroxybenzaldehyde (5.0 g, 21.4 mmol) was added at room temperature to a solution of N-methyl-3-picolylamine (2.6 g, 21.6 mmol) and diethyl phosphite (3.0 g, 21.6 mmol) in 20 ml toluene. The reaction mixture was stirred at room temperature for 2 h then refluxed for 15 min. After the evaporation of toluene, the residue was column chromatographed using 95/5 CHCl₃/MeOH as eluent. An amount of 4.4 g of title compound was isolated, yield =43%. IR (film): 3640 cm⁻¹: OH, 1480: C=N, pyridine, 1430: tert-Bu, 1240: P=O, 1040: P—O—C. NMR (CDCl₃): δ=8.52, 7.77 and 7.27 (3 m, 4H): aromatic H, 3-picolyl 7.25 (d, J$_{P-H}$=2 Hz, 2H): aromatic H, 3,5-di-t-butyl-4-hydroxyphenyl 5.29 (s, 1H): OH 4.20, 3.90 and 3.70 (3 m, 4H): P—O—CH₂—CH₃ 3.90 (d, J$_{P-H}$=23.5 Hz, 1H): CH—PO₃Et₂ 3.90 and 3.37 (2d, J=13.5 Hz, 2H): N(CH₃)—CH₂—Py 2.42 (s, 3H): N(CH₃)—CH₂—Py 1.45 (s, 18H): tert-Bu 1.37 and 0.99 (2t, J=7 Hz, 6H): P—O—CH₂—CH₃ MS: m/e=477: M++1,339: M+—PO₃Et₂

EXAMPLE 7 (compound 29)

Diethyl α-(3,5-di-tert-butyl-4-hydroxyphenyl)-N-(1-phenylethyl)-aminomethyldiphosphonate

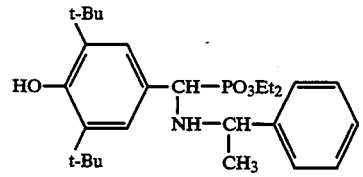

The process described in example 4 was used. The title compound was isolated by column chromatography using 98/2 CHCl₃/MeOH as eluent. Yield: 54%, mp=95°-110° C. IR (film): 3620 cm⁻¹: OH, 3300 (broad): NH, 1430: tert-Bu, 1230: P=O, 1150: P—O—Et, 1020: P—O—C. NMR (CDCl₃): mixture of diastereoisomers δ=7.27 (m, 5H): H phenyl 7.09 (d, J$_{P-H}$=2 Hz, 2H): aromatic H, 3,5-di-t-butyl-4-hydroxyphenyl 5.16 (s, 1H): OH 4.14, 3.90 and 3.80 (3 m, 4H): P—O—CH₂—CH₃ 4.00 (d, J$_{P-H}$=19 Hz, 1H): CH—PO₃Et₂ 3.70 (q, J=6 Hz, 1H): NH—CH—Ph CH₃ 2.0 (broad): NH—1.42 (s, 18H): tert-Bu 1.35 (d, J=6 Hz, 3H): NH—CH—Ph CH₃ 1.33 and 1.07 (2t, J=7 Hz, 6H): P—O—CH₂CH₃MS: m/e=338: M+—PO₃Et₂

EXAMPLE 8 (compound 38) Diethyl α-(3,5-di-tert-butyl4-hydroxyphenyl)-N-piperonyl-aminomethylphosphonate

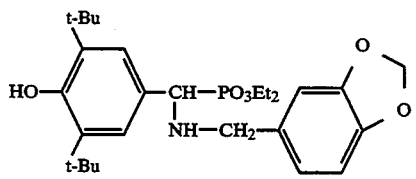

The process described in example 1 was used. The title compound was purified by column chromatography using 98/2 CHCl₃/MeOH as eluent. Yield =77%, mp=122.5°-123.5° C. IR (film): 3640 cm⁻¹: OH, 3340: NH, 1440: tert-Bu, 1250: P=O, 1030: P—O—C. NMR (CDCl₃): δ=7.19 (d, J$_{P-H}$=2 Hz, 2H): aromatic H, 3,5-di-tert-butyl-4-hydroxyphenyl 6.80 (d, J=1.5 Hz, 1H), 6.75 (d, J=8 Hz, 1H) and 6.69 (dxd, J=1.5, J=8 Hz, 1H): aromatic H, piperonyl 5.95 (s, 2H): methylenedioxy 5.20 (s, 1H): OH 4.80, 3.95 and 3.83 (3 m, 4H): P—O—CH₂—CH₃ 3.91 (d, J$_{H-P}$=19 Hz, 1H): CH—PO₃Et₂ 3.73 and 3.50 (2d, J=13 Hz, 2H):

NH—CH₂—Ar 2.04 (large): NH—1.46 (s, 18H): tert-Bu 1.30 and 1.12: (2t, J=7 Hz, 6H): P—O—CH₂—CH₃ MS: m/e=505: M⁺, 368: M⁺—PO₃Et₂. Elemental analysis C₂₇H₄₀NO₆P % Calc. C 64.14 H 7.95 N 2.77 P 6.10 % Found C 64.41 H 8.07 N 2.73 P 6.21

EXAMPLE 9 (compound 73)

Diethyl α-(3,5 di-sec-butyl-4-hydroxyphenyl)-N-(2-phenylethyl) aminomethylphosphonate

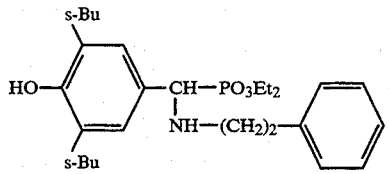

The starting compound 3,5-di-sec-butyl-4-hydroxybenzaldehyde was prepared by formylation of 2,6-di-sec-butylphenol, mp=65°–68° C., IR (KBr): 2740 cm⁻¹: (CHO), 1650: C=O.

The process described in example 1 was used to prepare the title compound which was purified by column chromatography (95/5 CHCl₃/MeOH). Yield 68%. IR (film) 3300 cm⁻¹: OH, 1460: CH₂ and CH₃, 1200: P=O, 1160: P—O—Et, 1030: P—O—C. NMR (CDCl₃): δ=7.20 (m, 5H): phenyl H 6.97 (d, 2H): aromatic H, 3,5-di-sec-butyl-4-hydroxyphenyl 4.90 (s, 1H): OH 3.95 and 3.73 (2 m, 4H): P—O—CH₂—CH₃ 3.97 (d, J$_{P-H}$=19 Hz, 1H): CH—PO₃Et₂ 2.88 (m, 2H), 1.60 (m, 4H), 1.22 (m, 6H) and 0.86 (m, 6H): sec-Bu 2.77 (m, 4H): NH—(CH₂)₂—Ph 1.88 (large): NH—1.23 and 1.09 (2t, J=7 Hz, 6H): P—O—CH₂-CH₃ MS: m/e=338:-M⁺—PO₃Et₂ Elemental analysis C₂₇H₄₂NO₄P % Calc. C 68.20 H 8.90 N 2.90 P 6.50 % Found C 68.04 H 9.15 N 3.13 P 6.36

EXAMPLE 10 (compound 45) Diethyl α-(3,5-di-tert-butyl-4-hydroxyphenyl)-N-(1-phenyl cyclopentyl)-aminomethylphosphonate

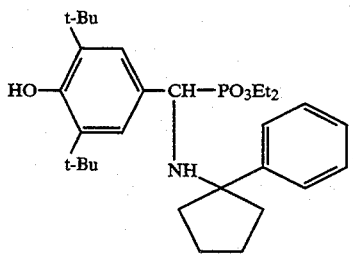

1-Phenyl-cyclopentylamine was prepared according to Organic Syntheses, Coll Vol VI, p. 9 10, John Wiley & Sons, 1988. A mixture of 5.0 g (21.37 mmol) 3,5-di-tert-butyl-4-hydroxybenzaldehyde and 3.5 g (21.5 mmol) 1-phenyl-cyclophentylamine dissolved in 30 ml THF to which 2 g of 3 Å molecular sieve was added, was stirred overnight. The molecular sieve was filtered and the THF was evaporated. Diethyl phosphite (3.0 g, 21.50 mmol) was added to the residue and the mixture was heated to 140° for 5 h. The title compound was isolated by column chromatography (95/5 CHCl₃/MeOH) and recrystallized in petroleum ether: 3.9 g were obtained, yield 35%, mp=114°–115° C. IR (KBr): 3620 cm⁻¹: OH, 3300: NH, 1430: tert-Bu, 1200: P=O, 1030: P—O—C. NMR (CDCl₃): δ=7.20 (m, 5H): H phenyl 6.92 (d, J$_{P-H}$=2 Hz, 2H): aromatic H, 3,5-di-tert-butyl[-4-hydroxyphenyl 5.05 (s, 1H): OH 3.97, 3.74 and 3.45 (3 m, 4H): P—O—CH₂—CH₃ 3.60 (d, J$_{P-H}$=23 Hz, 1H): CH—PO₃Et₂ 1.85 (broad): NH—1.50-2.10 (m, 8H): H, cyclopentylidene 1.37 (s, 18H): tert-Bu 1.24 and 0.94 (2t, J=7 Hz, 6H): P—O—CH₂—CH₃ MS: m/e=378:M⁺—PO₃Et₂

EXAMPLE 11 (compound 43) Diethyl α-(3,5-di-tert-butyl-4-hydroxyphenyl)-N-[2-(2-pyridyl)-ethyl]aminomethyl-phosphonate

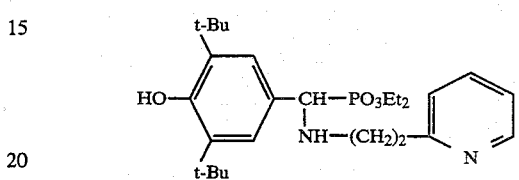

The process described in example 1 was used. The title compound was purified by column chromatography (9/1 CHCl₃/MeOH) and recrystallized in petroleum ether 40–60. Yield 81%, mp=76°–78° C. IR(film): 3640 cm⁻¹: OH, 3300: NH, 1590, 1570, 1470: -2Py, 1430: tert-Bu, 1230: P=O, 1160: P—OEt, 1020: P—O—C. NMR (CDCl₃): δ=8.47, 7.53 and 7.09 (3 m, 4H): aromatic H, 2-pyridyl 7.12 (d, J$_{P-H}$=2 Hz, 2H): aromatic H, 3,5-di-t-butyl-4-hydroxyphenyl 5.15 (s, 1H): OH 3.94 (d, J$_{P-H}$=19 Hz, 1H): CH—PO₃Et₂ 3.86 (m, 4H): P—O—CH₂—CH₃ 2.92 (m, 4H): NH—(CH₂-)₂—Py 2.15 (broad): NH—1.38 (s, 18H): tert-Bu 1.19 and 1.05 (2t, J=7 Hz, 6H): P—O—CH₂CH₃ MS: m/e=477: M⁺ +1,339: M⁺—PO₃Et₂ Elemental analysis C₂₆H₄₁N₂O₄P % Calc. C 65.52 H 8.67 N 5.88 P 6.50 % Found C 65.33 H 8.52 N 5.69 P 6.62

EXAMPLE 12 (compound 80) Diethyl α-(3,4t-methylenedioxyphenyl)-N-(3-phenylpropyl)-aminomethylphosphonate

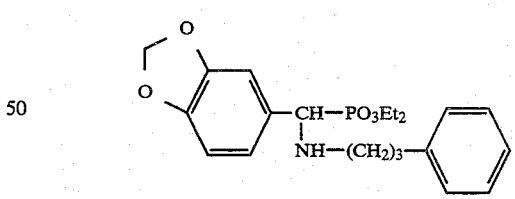

The process described in example 10 was followed. The title compound was purified by column chromatography using 9/1 CHCl₃/MeOH as eluent. Yield 68%. IR (film): 3300 cm⁻¹: NH, 1240: P=O, 1020: P—O—C. NMR (CDCl₃): δ=7.25 and 7.15 (2 m, 5H): phenyl H 6.95, 6.83 and 6.77 (3 m, 3H): aromatic H, 3,4-methylenedioxyphenyl 5.95 (s, 2H): methylenedioxy 4.11, 4.00 and 3.89 (3 m, 4H): P—O—CH₂—CH₃ 3.92 (d, J$_{P-H}$=19.5 Hz, 1H): CH—PO₃Et₂ 2.58 (m, 4H): NH—CH₂—CH₂—CH₂Ph 1.75 (broad): NH—1.77 (m, 2H): NH—CH₂—CH₂—CH₂Ph 1.30 and 1.19 (2t, J=7 Hz, 6H): P—O—CH₂CH₃ MS: m/e=404 M⁺−1

EXAMPLE 13 (compound 7) Diethyl α-(3,5-di-tert-butyl-4-hydroxyphenyl)-N-(4-methoxyphenyl)-aminomethylphosphonate

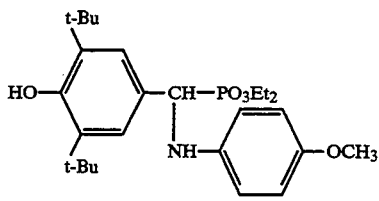

A mixture of 5 g (21.4 mmol) 3,5-di-tert-butyl-4-hydroxybenzaldehyde and 2.66 g (21.6 mmol) 4-methoxyaniline in 30 ml of THF was reacted overnight on 3 Angstrom molecular sieves. Molecular sieve was filtrated, THF was evaporated then 2.98 g (21.6 mmol) diethyl phosphite was added. The reaction mixture was heated at 140° C. for 6 h then purified by column chromatography (98/2 CHCl$_3$/MeOH ). A white solid weighing 8.6 g was obtained, yield 83%, mp=108°-109° C. IR (film) 3640 cm$^{-1}$:OH, 3400 (broad): NH, 1520: Phenyl, 1430: tert-Bu, 1240: P=O, 1030: P—O—C. NMR (CDCl$_3$): δ=7.20 (d, $J_{P-H}$=2 Hz, 2H). aromatic H, 3,5-di-tert-butyl-hydroxyphenyl 6.65 (2d, J=9 Hz, 4H): aromatic H, 4-methoxyphenyl 5.15 (s, 1H): OH 4.60 (d, $J_{P-H}$=23 Hz, 1H): CH—PO$_3$Et$_2$ 4.10, 3.90 and 3.60 (3 m, 4H): P—O—CH$_2$—CH$_3$ 3.70 (s, 1H): —OCH$_3$ 1.80 (broad): NH 1.40 (s, 18H): tert-Bu 1.25 and 1.05 (2t, J=7 Hz, 6H) P—O—CH$_2$—CH$_3$ MS: m/e 478: M$^+$ +1,447: M$^+$, 341: M$^+$—PO$_3$Et$_2$+H. Elemental analysis C$_{26}$H$_{40}$NO$_5$P % Calc. C 65.40 H 8.40 N 2.90 P 6.50 % Found C 65.34 H 8.54 N 2.97 P 6.64

EXAMPLE 14 (compound 60)
Diethyl α-(3,5-di-tert-butyl-4-hydroxyphenyl)-N-acetyl-N-(3-phenylpropyl)-aminomethylphosphonate

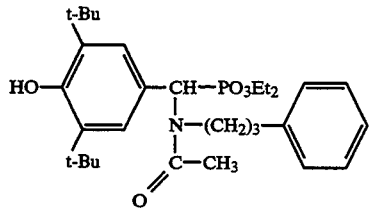

Acetic anhydride (17.5 g, 0.172 mol) was added to a solution of 80 g (0.164 mol) diethyl α-(3,5-di-tert-butyl-4-hydroxyphenyl)-N-(3-phenylpropyl)aminomethylphosphonate and 17.35 g (0.172 mol) triethylamine in 450 ml toluene. The reaction mixture was heated to reflux for 6 h then was extracted with brine and finally dried over MgSO$_4$. After evaporation to dryness, the residue was recrystallized in a mixture of acetone and tert-butyl methyl ether. 59 g were obtained, yield 68%, mp=135°-136° C.

The title compound can also be obtained by using acetyl chloride as acylating agent. Acetyl chloride (0.28 g, 3.62 mmol) was added to a solution containing 1.77 g (3.62 mmol) aminophosphonate and 0.36 g (3.62 mmol) triethylamine. After heating at reflux temperature work-up was carried out as described above. 2.2 g was obtained, yield 70%, mp=134°-136° C. Elemental analysis C$_{30}$H$_{46}$NO$_5$P % Calc. C 67.80 H 8.61 N 2.64 % Found C 67.76 H 8.61 N 2.50 IR (KBr): 1620 cm$^{-1}$: C=O, 1425: tert-Bu, 1230: P=O, 1020: P—O—C. MS: m/e=532: M$^+$+1,488: M$^+$—CH$_3$CO, 394: M$^+$—PO$_3$Et$_2$ RMN (CDCl$_3$): mixture of two amide rotation isomers. The characteristics of the major isomer are reported here δ=7.47 (s, 2H): aromatic H, 3,5-di-tert-butyl-4-hydroxyphenyl 7.15 and 6.94 (2 m, 5H): phenyl H 6.28 (d, $J_{P-H}$=22 Hz, 1H): CH—PO$_3$Et$_2$ 5.3 (s, 1H): OH 4.1 (m, 4H): P—O—CH$_2$—CH$_3$ 3.59 and 3.42 (2 m, 2H): NH—CH$_2$—(CH$_2$)$_2$—Ph 2.32 (t, J=8 Hz, 2H): NH—(CH$_2$)$_2$—CH$_2$—Ph 2.06 (s, 3H): CO—CH$_3$ 1.42 (s, 18H): tert-Bu 1.32 and 1.14 (2t, J=7 Hz, 6H): P—O—CH$_2$—CH$_3$ 1.60 and 0.93 (2 m, 2H): NH—CH$_2$—CH$_2$—CH$_2$—Ph

EXAMPLE 15 (compound 64)
Diethyl α-(3,5-di-tert-butyl-4-hydroxyphenyl)-N-trifluoroacetyl-N-(3-phenylpropyl)-aminomethylphosphonate

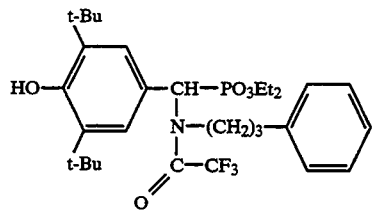

Trifluoroacetic anhydride (1.03 g, 4.9 mmol) was added under nitrogen to a mixture of 2.0 g (4.1 mmol) of diethyl α-(3,5-di-tert-butyl-4-hydroxyphenyl)-N-(3-phenyl propyl)-aminomethylphosphonate and 0.4 g (4.1 mmol) of triethylamine in 20 ml benzene. The mixture was heated to 40° C. for 1 h, evaporated to dryness and the residue was recrystallized in petroleum ether. 2.3 g of a white solid was obtained, yield 96%; mp=74°-79° C.

EXAMPLE 16 (compound 27) Diethyl α-(3,5-di-tert-butyl-4-hydroxyphenyl)-N-(4-phenylbutyl)-aminomethylphosphonate

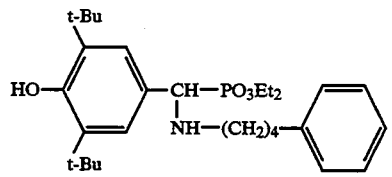

The process described in example 1 was employed using 4-phenylbutylamine as amine. A white solid was obtained with a yield of 51%, after purification by column chromatography (98/2 CHCl$_3$/MeOH), mp=93°-94° C. IR (KBr) 3400 cm$^{-1}$: NH, 1430: tert-Bu, 1220: P=O, 1030: P—O—C. NMR (CDCl$_3$) δ=7.25 and 7.15 (2 m, 5H): phenyl H 7.17 (d, $J_{P-H}$=2 Hz, 1H): aromatic H, 3,5-di-t-butyl-4-hydroxyphenyl 5.2 (s, 1H): OH 4.06, 3.92 and 3.78 (3 m, 4H): P—O—CH$_2$—CH$_3$ 3.90 (d, $J_{P-H}$=19 Hz, 1H): CH—PO$_3$Et$_2$ 2.56 (m, 4H): NH—CH$_2$—(CH$_2$)$_2$—CH$_2$—Ph 1.74 (broad): NH—1.65 and 1.50 (2 m, 4H): NH—CH$_2$—(CH$_2$)$_2$—CH$_2$—Ph 1.42 (s, 18H): tert-Bu 1.26 and 1.12 (2t, J=7 Hz, 6H): P—O—CH$_2$—CH$_3$ MS: m/e=366:M$^+$—PO$_3$Et$_2$ Elemental analysis C$_{29}$H$_{46}$NO$_4$P % Calc. C 69.20 H 9.20 N 2.80 P 6.10 %
Found C 69.01 H 9.45 N 2.93 P 6.27

EXAMPLE 17 (compound 40)

Diethyl α-(3,5-di-tert-butyl-4-hydroxyphenyl)-N-(3,5-di-tert-butyl-4-hydroxybenzyl)-aminomethylphosphonate

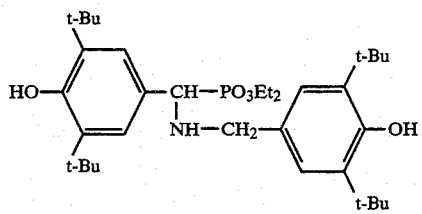

A mixture of 0.97 g (4.13 mmol) 3,5-di-tert-butyl-4-hydroxybenzaldehyde and 1.0 g (4.25 mmol) 3,5-di-tert-butyl-4-hydroxybenzylamine (mp=158°-163° C., prepared according to E. Miller et al, *Chem. Ber.* 92, 2278-2293, 1959) in 20 ml THF was stirred at room temperature overnight. It was dried over MgSO$_4$ then evaporated. A solution of the obtained imine in 10 ml toluene is reacted with 0.42 g (4.16 mmol) triethylamine and 0.57 g (4.25 mmol) diethyl phosphite at 100° C. for 6 h. After evaporation the residue was purified by two column chromatographies (SiO$_2$, 95/5 then 98/2 CHCl$_3$/MeOH). An amount of 0.4 g (16%) of a white solid was obtained, mp=120°-123° C. IR (KBr) 3640 cm$^{-1}$: OH, 3400 (broad): NH, 1440: tert-Bu, 1240: P=O, 1030: P—O—C. NMR (CDCl$_3$): δ=7.20 (d, J$_{P-H}$=2 Hz, 2H): aromatic H, -substituted 3,5-di-t-butyl-4-hydroxyphenyl 7.05 (s, 2H): aromatic H, 3,5-di-tert-butyl-4-hydroxy benzylamino 5.18 and 5.14 (2s, 2H)=OH of the two phenols 4.06, 3.94 and 3.80 (3 m, 4H): P—O—CH$_2$—CH$_3$ 3.97 (d, J$_{P-H}$=19 Hz, 1H): CH—PO$_3$Et$_2$ 3.72 and 3.48 (2d, J =12.5 Hz, 2H): NH—CH$_2$—Ph 1.44 and 1.42 (2s, 36H): 4 groups tert-Bu 1.27 and 1.12 (2t, J=7 Hz, 6H): P—O—CH$_2$CH$_3$ MS: m/e=452:M+—PO$_3$Et$_2$

EXAMPLE 18 (compound 68) Diethyl α-(3,5-di-tert-butyl-4-hydroxybenzyl)-N-(3-phenylpropyl)-aminomethylphosphonate

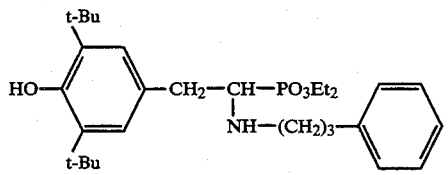

3,5-Di-tert-butyl-4-hydroxyphenylacetaldehyde was obtained by reduction of ethyl 3,5-di-tert-butyl-4-hydroxyphenylacetate with a double molar excess of diisobutyl aluminum hydride in hexane at −78° C., mp=74°-76° (MS =m/e: 248=M+, 219=M+—CHO).

The above described aldehyde (4 g, 15.3 mmol) was reacted with 3-phenylpropylamine (2.1 g, 15.5 mmol) in 50 ml THF at room temperature for 18 h. After drying and solvent evaporation, diethyl phosphite (2.2 g, 15.5 mmol) was added and the mixture was heated at 140° C. for 5 h. Purification by column chromatography (98/2 CHCl$_3$/MeOH) gave 2.38 g (31%) of a light yellow oil. IR (film) 3640 cm$^{-1}$: OH, 3300 (broad): NH, 1440: tert-Bu, 1230: P=O, 1030 P—O—C NMR (CDCl$_3$): δ=7.20, 7.13 and 7.0 (3 m, 5H): phenyl H 7.03 (s, 2H): aromatic H, 3,5-di-tert-butyl-4-hydroxyphenyl 5.20 (s, 1H): OH 4.14 (m, 4H): P—O—CH$_2$—CH$_3$ 3.08 (m, 2H): NH—CH$_2$—(CH$_2$)$_2$—Ph 2.72 (m, 2H): Ph—CH$_2$—CH—PO$_3$Et$_2$ 2.50 (dxt, J$_{P-H}$=12 Hz, J=7.5 Hz, 1H): CH—PO$_3$Et$_2$ 2.42 (t, J=7 Hz, 2H): NH—(CH$_2$)$_2$—CH$_2$—Ph 1.58 (m, 2H): NH—CH$_2$—CH$_2$—CH$_2$—ph 1.42 (s, 18H): tert-Bu 1.32 and 1.29 (2t, J=7 Hz, 6H): P—O—CH$_2$—CH$_3$ MS: m/e=504: M++1,366: M+—PO$_3$Et$_2$

EXAMPLE 19 (compound 67)

Diethyl α-(3.5-di-tert-butyl-4-methoxyphenyl)-N-(3-phenylpropyl)-aminomethylphosphonate

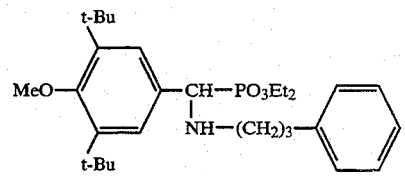

A mixture containing 2 g (9.7 mmol) 2,6-di-tert-butyl phenol, 0.4 g NaOH dissolved in 4 ml water, 13.7 g (60.1 mmol) benzyl triethyl ammonium chloride and 12 g (84.5 mmol) methyl iodide was heated at 45° for 18 h. After purification 0.67 g 2,6-di-tert-butyl anisol was obtained. This compound (1.46 g, 6.63 mmol) was formylated by reaction at 0° C. with dichloromethyl methyl ether (1.15 g, 10 mmol) in presence of tin tetrachloride (3.1 g, 11.9 mmol) in 20 ml CH$_2$Cl$_2$. After hydrolysis and extraction into ether, 1.15 g of 3,5-di-tert-butyl-4-methoxybenzaldehyde were obtained (MS: m/e=248: M+; 233=M+—CH$_3$).

This aldehyde was reacted with 0.63 g (4.68 mmol) 3-phenylpropylamine in 25 ml THF, then 0.65 g (4.68 mmol) diethylphosphite was added and the resulting mixture heated at 110° C. for 4 h. Purification by column chromatography gave 0.9 g (37% of a yellow oil). IR (film) 3400 cm$^{-1}$(broad): NH, 1440: tert-Bu, 1220: P=O, 1020: P—O—C. NMR (CDCl$_3$): δ=7.24 and 7.14 (2 m, 5H) phenyl H 7.26 (d, J$_{P-H}$=2 Hz, 2H): aromatic H, 3,5 di-tert-butyl-4-hydroxyphenyl 4.05, 3.93 and 3.79 (3 m, 4H): P—O—CH$_2$—CH$_3$ 3.95 (d, J$_{P-H}$=19 Hz, 1H): CH—PO$_3$ET$_2$ 3.66 (s, 3H): Ph—O—CH$_3$ 2.66 and 2.59 (2 m, 4H): NH—CH$_2$—CH$_2$—CH$_2$—Ph 1.79 (m, 3H): NH and NH—CH$_2$—CH$_2$—CH$_2$—Ph 1.42 (s, 18H): tert-Bu 1.27 and 1.10 (2t, J=7 Hz, 6H): P—O—CH$_2$—CH$_3$ MS: m/e=504: M++366:M+—PO$_3$Et$_2$

EXAMPLE 20 (compound 84)

Diethyl α-(3,5-di-tert-butyl-4-hydroxyphenyl)-N-allyl-aminomethylphosphonate

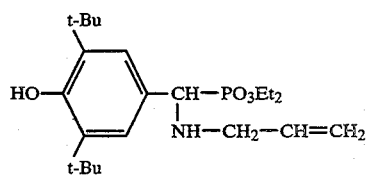

3,5-Di-tert-butyl-4-hydroxybenzaldehyde (10.0 g, 43 mmol) was reacted at room temperature with allyl amine (2.45 g, 43 mmol) in 20 ml THF overnight. The solution was dried over MgSO4 and evaporated to dryness.

The reagent diethyl trimethylsilylphosphite was prepared by adding chloro trimethylsilane (5.1 g, 47 mmol) dissolved in 10 ml CH2Cl2 into a solution cooled to 0° C. containing HPO3Et2 (5.9 g, 43 mmol), Et3N (4.7 g, 47 mmol) in 40 ml CH2Cl2. The mixture was stirred at 0° C. for 20 min, then the previously described imine dissolved in 70 ml CH2Cl2 was added. The reaction mixture was left to reach room temperature and was stirred for 5 h. Hydrolysis was carried out with 100 ml water and the aqueous phase was extracted with CH2Cl2. The pooled organic phases were dried over K2CO3. The crude compound (21.0 g) was purified by column chromatography (98/2 CHCl3/MeOH), 16.0 g were obtained, yield 90%; mp=91°-92° C. IR (film): 3640 cm$^{-1}$:OH, 3300 (broad): NH, 1430: tert-Bu, 1230: P=O, 1020: P—O—C MS m/e=411: M+, 274: M+—PO3Et2 NMR (CDCl3): δ=7.20 (s, 2H): aromatic H, 3,5-di-tert-butyl-4-hydroxyphenyl 5.85 (m, 1H): NH—CH2—CH=CH2 5.19 (s, 1H): OH 5.12 (m, 2H):NH—CH2—CH=CH2 3.98 (d, J$_{P-H}$=18.5 Hz, 1H): CH—PO3Et2 3.93 (m, 4H): P—O—CH2—CH3 3.18 (m, 2H): NH—CH2—CH=CH2 1.88 (broad, 1H): NH—CH2—CH=CH2 1.43 (s, 18H): tert-Bu 1.28 and 1.12 (2t, J=7 Hz, 6H); P—O—CH2—CH3

EXAMPLE 21 (compound 84)
α-(3,5-Di-tert-butyl-4-hydroxyphenyl)-N-(3-phenylpropyl)-aminomethylphosphonic acid

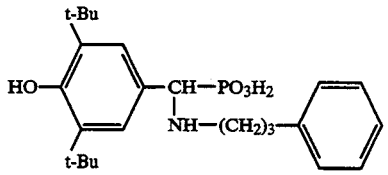

Diethyl α-(3,5-di-tert-butyl-4-hydroxyphenyl)-N-(3-phenylpropyl)aminomethylphosphonate (compound 22, 3.0 g, 6.1 mmol) was heated at reflux in 30 ml NHCl for 24 h. The compound was extracted with chloroform, 2.5 g were obtained. Yield =94%, mp=162°-169° C. IR (KBr) 3640 cm$^{-1}$: OH, 3400 (broad): NH, 2800 and 1600: PO-H, 1430: tert-Bu, 1200: P=O, 1000 and 940: P—OH Elemental analysis: C24H36NO4P. % Calc. C 66.49 H 8.37 N 3.23 P 7.14 % Found C 66.69 H 8.52 N 2.95 P 6.91 0.2 % H2O The structure of the compound was confirmed by titration.

EXAMPLE 22 (compound 83)
Diethyl α-(3,5-di-tert-butyl4-hydroxyphenyl)-aminomethylphosphonate

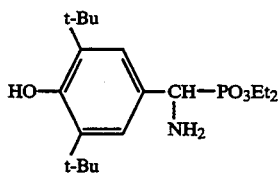

Diethyl α-(3,5-di-tert-butyl-4-hydroxyphenyl)-N-(1-phenylethyl)-aminomethylphosphonate, compound 29 (3.0 g, 6.3 mmol) was hydrogenated in ethanol with 3.0 g 10% Pd/C. The compound was purified by column chromatography (9/1 CHCl3/MeOH): 1.5g was obtained; yield =62%, mp=131°-133° C.

The title compound was also obtained by catalytic hydrogenation (10% Pd/C), EtOH) of diethyl α-(3,5-di-tert-butyl-4-hydroxyphenyl)-N-(1-phenylcyclopentyl) aminophosphonate (compound 45) or diethyl α-(3,5-di-tert-butyl-4-hydroxyphenyl)-N-benzyloxycarbonyl-amino methylphosphonate (compound 85) IR (KBr) 3300 and 3360 cm$^{-1}$: NH2, 1440: tert-Bu, 1170: P=O, 1030: P—O—C NMR (CDCl3): δ=7.24 (d, J$_{P-H}$=2 Hz, 2H): aromatic H, 3,5 di-tert-butyl-4-hydroxyphenyl 5.21 (s, 1H): OH 4.17 (d, J$_{P-H}$=16 Hz, 1H): CH—PO3Et2 3.94 (m, 4H): P—O—CH2—CH3 1.77 (broad. 2H): NH2 1.44 (s, 18H): tert-Bu 1.28 and 1.15 (2xt, J=7 Hz, 6H): P—O—CH2—CH3 MS: m/e=234:- M+—PO3Et2

EXAMPLE 23 (compound 85) Diethyl α-(3,5-di-tert-butyl-4-hydroxyphenyl)-N-benzyloxycarbonyl-aminomethylphosphonate

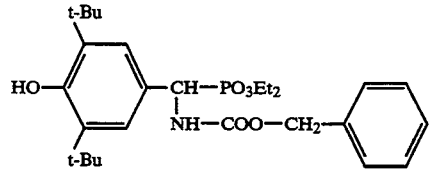

In a flask were mixed acetic acid (17.0 g, 282 mmol) and thionyl chloride (10.0 g, 83 mmol). Then were added sequentially benzyl carbamate (3.0 g, 20 mmol), diethyl phosphite (2.8 g, 20 mmol) and 3,5-di-tert-butyl-4-hydroxybenzaldehyde (5.0 g, 21.3 mmol). The mixture was stirred at room temperature for 20 min then at 80° C. for 2 h. The mixture was left to cool, then was dissolved in CHCl3 and was extracted successively with H2O, 20% NaOH and H2O. The crude compound was extracted hot with ethyl acetate and the pure crystals were filtered, 6.0 g were obtained, yield 60%, mp=196°-197° C. IR (KBr) 3520 Cm$^{-1}$: OH, 3240: NH, 1690: C=O, 1530: amide II, 1430: tert-Bu, 1230: P=O, 1110: C—N, 1030: P—O—C. NMR (CDCl3): δ=7.33 (m, 5H): aromatic H, NHCOO—CH2—Ph 7.18 (s, 2H): aromatic H, 3,5-di-tert-butyl-4-hydroxyphenyl 5.74 (m, 1H): CH—PO3ET2 5.22 (broad): NH—COOBz 5.15 and 5.08 (2xd, J=12,5 Hz, 2H): NH—COO—CH2—Ph 3.89 (m, 4H): P—O—CH2—CH3 1.42 (s, 18H): tert-Bu 1.27 and 1.06 (2xt, J=7 Hz, 6H): P—O—CH2—CH3 MS: m/e=505: M+, 368:M+—PO3Et2 Pharmacological studies performed in vivo have established that aminophosphonates of formula (I) are potent hypocholesterolemic compounds. Their antioxidant activity has also been clearly demonstrated in vitro. The antioxidant activity of aminophosphonates may be the basis for their use as inhibitors of platelet aggregation or hypoglycemic agents.

METHODS

A. Hypocholesterolemic activity

Mouse fed a normal diet is a convenient model which was proposed by several authors (P. Olivier et al, Atherosclerosis 70, 107–114, 1988) ,for the screening for hypocholesterolemic drugs. OF1 strain mice (Iffa Credo)

weighing between 25 and 35 g were divided into 5 groups of 5 animals each, four groups received the test compounds and the fifth group served as control. The test compounds were dissolved in diethyl ether. The ether solution was added to food to obtain a final concentration of 0.1%. compound in food. Ether was then evaporated at room temperature. The animals were fed for 10 days, the daily food intake corresponds to ca. 180 mg/kg. After an overnight fast, they were sacrificed by decapitation under ether anesthesia. Blood samples were collected using EDTA as anticoagulant.

Plasma cholesterol was measured by an enzymatic test (DIAMED, Morat, Switzerland). The mean values of each group receiving the test or reference compounds were expressed as percent of mean value of the contemporary control.

B. Antioxidant activity

The liver of a Wistar rat anesthetized with ether was collected and homogenized in 4 volumes of phosphate buffer (+4° C., pH 7.4) by means of a Potter. After centrifugation at 2000 rpm for 10 min the supernatant obtained was kept at +4° C. Lipid peroxidation was carried out in presence of FeSO4 according to the method described by A. T. Quitaniha et at, *Ann. N.Y. Acad. Sci.*, 393, 32–47, 1982.

The mixture contained 1.7 ml phosphate buffer, 0.2 ml homogenate and 0.1 ml of a 2 mM FeSO$_4$ solution. The test compounds were added in a volume of 61 µl of ethanol or DMSO. Oxydation was carried out at 37° C. for 2 h and was stopped by the addition of 20 µl of 2% ethanolic solution of BHT. Generated peroxides were measured using thiobarbituric acid according to the method described by Yagi (in "Lipid Peroxides in Biology and Medicine", p. 223–242, 1982, Ed. K. Yagi, Academic Press Inc.) using 1,1,3,3-tetramethoxypropane as standard.

In a first step, the compounds were tested at the concentration of 25 µM. For most compounds which displayed an inhibition superior to 50% of the iron induced oxidation at a concentration of 25 µM, the dose inhibiting peroxidation by 50% (IC$_{50}$) was determined by sequential dilutions of the product between $10^{-7}$ and $10^5$M. In cases where IC$_{50}$ was not determined the only <25 µM mention is specified. Compounds whose IC$_{50}$ are inferior to 25 µM are considered as having a significant antioxidant activity.

RESULTS

The values listed on table 1 show that a great number of aminophosphonates of formula (I) are remarkable hypocholesterolemic agents in the mouse.

In particular, compounds 3, 7, 9, 17, 19, 21, 22, 27, 29, 38, 42, 43, 60, 61, 62, 73 decrease plasma cholesterol by more than 30% and can be considered more active than known hypocholesterolemic agents. In the same experimental conditions, Clofibrate, Gemfibrozil and Fenofibrate, which are drugs used clinically for treatment of hyperlipidemia, have respectively the following plasma cholesterol values of +4%, −7%, −26% as compared to control. The antioxidant product BHT, 2,6-di-tert-butyl-4-methylphenol, has no hypocholesterolemic activity in this model.

Regarding the mechanism of hypocholesterolemic activity, the aminophosphonates studied were found inactive on the enzyme HMGCoA reductase at 10 µM concentration. These results were confirmed by the absence of effect of these compounds on the incorporation of $^{14}$C acetate in cholesterol synthesized by Hep G2 cells and CaCo-2 at doses up to 10 µM. In these two tests the positive control Lovastatin (hypocholesterolemic drug with HMGCoA reductase inhibitory activity) inhibits the enzyme and the $^{14}$C acetate incorporation by more than 98%. The mechanism of hypocholesterolemia of this class is different and potentially unique.

Furthermore the above-mentioned aminophosphonates display at the same time an in vitro antioxidant activity which is superior to that of the drug Probucol and which is comparable to BHT, an established antioxidant: IC$_{50}$ (Probucol)>25 µM; IC$_{50}$ (BHT)=5 µM. The hypocholesterolemic drugs from the fibrate family did not display any measurable antioxidant activity in this test.

In conclusion the aminophosphonates tested display simultaneously a hypocholesterolemic and antioxidant activity which are remarkable.

The aminophosphonates of formula (I) can thus be used for the treatment of . hyperlipidemia and can be administered preferably in the form of capsules, tablets and granules. For this purpose the active principle should be mixed with a pharmaceutical carrier.

As used herein, the term "pharmaceutical carrier" denotes a solid or liquid filler, diluent or encapsulating substance. Some examples of the substances which can serve as pharmaceutical carriers are sugars, starches, cellulose and its derivatives, ethyl cellulose, cellulose acetate, powdered tragacanth, malt, gelatin, talc, stearic acid, magnesium stearate, calcium sulphate, vegetable oils, polyols and polyethylene glycol, agar, alginic acid, pyrogen-free water, isotonic saline and phosphate buffer solutions, as well as other non-toxic compatible substances used in pharmaceutical formulations. Wetting agents and lubricants such as sodium lauryl sulphate, as well as colouring agents, flavouring agents and preservatives, can also be present.

The pharmaceutical carrier employed in conjunction with the phosphonates is used at a concentration sufficient to provide a practical size to dosage relationship. Preferably the pharmaceutical carrier comprises from about 0.1% to 99% by weight of the total composition. Capsules and tablets are prepared by conventional methods using aminophosphonates in their liquid or crystalline form as described in the following examples:

| Example of a Capsule Formulation | |
|---|---|
| Ingredients | mg/Capsule |
| Compound 73 | 300 |
| Gelatin | 100 |
| Polyethylene glycol 1000 | 600 |
| Potassium sorbate | 0.5 |

| Example of a Tablet Formulation | |
|---|---|
| Ingredients | mg/Tablet |
| Compound 22 | 500 |
| Hydroxypropyl methyl cellulose | 500 |
| Magnesium stearate | 3 |

For the treatment of specific disease states, compositions containing a pharmaceutically acceptable aminophosphonate can be administered as a solution, suspension, emulsion or by intradermal, intramuscular, intravenous or intraperitoneal injection. Rectal administration of aminophosphonates can be performed by incorporating the active principle into conventional jelly bases to produce suppositories.

TABLE 1

Aminophosphonates substituted by phenol groups (I)

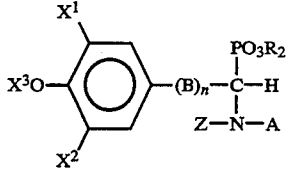

| Compound | Structure | mp (°C.) | Plasma Cholesterol (% Control) | Antioxidant Activity $IC_{50}$ ($\mu M$) |
|---|---|---|---|---|
| 1 | 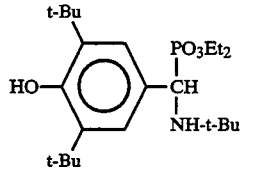 3,5-di-t-Bu-4-HO-C$_6$H$_2$-CH(PO$_3$Et$_2$)-NH-t-Bu | 49–51 | +8 | >25 |
| 2 | 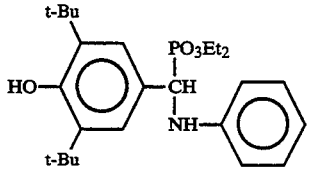 3,5-di-t-Bu-4-HO-C$_6$H$_2$-CH(PO$_3$Et$_2$)-NH-C$_5$H$_{11}$ | 90–91 | −8 | 2.5 |
| 3 | 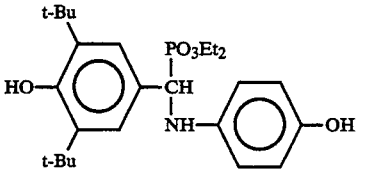 3,5-di-t-Bu-4-HO-C$_6$H$_2$-CH(PO$_3$Et$_2$)-NH-C$_6$H$_5$ | 124–125 | −30 | 5.1 |
| 4 | 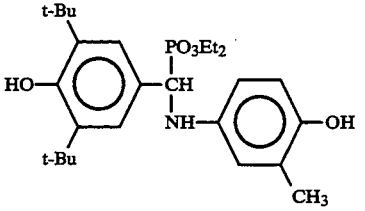 3,5-di-t-Bu-4-HO-C$_6$H$_2$-CH(PO$_3$Et$_2$)-NH-C$_6$H$_4$-OH | 69–70 | −15 | 4.1 |
| 5 | 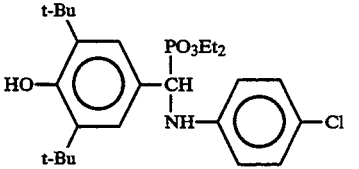 3,5-di-t-Bu-4-HO-C$_6$H$_2$-CH(PO$_3$Et$_2$)-NH-C$_6$H$_3$(OH)(CH$_3$) | wax | +2 | 1.3 |
| 6 | 3,5-di-t-Bu-4-HO-C$_6$H$_2$-CH(PO$_3$Et$_2$)-NH-C$_6$H$_4$-Cl | 132–134 | −17 | <25 |
| 7 | 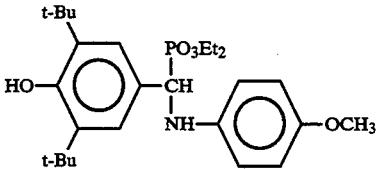 3,5-di-t-Bu-4-HO-C$_6$H$_2$-CH(PO$_3$Et$_2$)-NH-C$_6$H$_4$-OCH$_3$ | 108–109 | −47 | <25 |

TABLE 1-continued
Aminophosphonates substituted by phenol groups (I)

$$\text{structure (I): } X^3O\text{-phenyl(with } X^1, X^2\text{)-}(B)_n\text{-C(PO}_3R_2\text{)(H)-N(Z)-A}$$

| Compound | Structure | mp (°C.) | Plasma Cholesterol (% Control) | Antioxidant Activity IC$_{50}$ (μM) |
|---|---|---|---|---|
| 8 | 3,5-di-t-Bu-4-HO-phenyl-CH(PO$_3$Et$_2$)-NH-(3-CH$_3$-phenyl) | 146–147.5 | | <25 |
| 9 | 3,5-di-t-Bu-4-HO-phenyl-CH(PO$_3$Et$_2$)-NH-(4-OC$_2$H$_5$-phenyl) | 90–91 | −31 | <25 |
| 10 | 3,5-di-t-Bu-4-HO-phenyl-CH(PO$_3$Et$_2$)-NH-(4-C$_5$H$_{11}$-phenyl) | | +11 | 2.9 |
| 11 | 3,5-di-t-Bu-4-HO-phenyl-CH(PO$_3$Et$_2$)-NH-(3-CH$_3$-4-(5-chloro-phthalimido)-phenyl) | 166–168 | | 2.7 |
| 12 | 3,5-di-t-Bu-4-HO-phenyl-CH(PO$_3$Et$_2$)-NH-CH$_2$-phenyl | 99–100 | −23 | 0.7 |
| 13 | 3,5-di-t-Bu-4-HO-phenyl-CH(PO$_3$Et$_2$)-NH-(CH$_2$)$_2$-phenyl | 89–90 | −28 | 4.9 |
| 14 | 3,5-di-t-Bu-4-HO-phenyl-CH(PO$_3$Et$_2$)-NH-(CH$_2$)$_2$-(4-CH$_3$-phenyl) | 91–93 | −6 | <25 |

TABLE 1-continued

Aminophosphonates substituted by phenol groups (I)

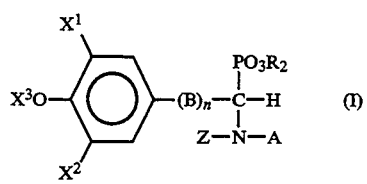

(I)

| Compound | Structure | mp (°C.) | Plasma Cholesterol (% Control) | Antioxidant Activity IC$_{50}$ (μM) |
|---|---|---|---|---|
| 15 | t-Bu, HO, t-Bu phenyl — CH(PO$_3$Et$_2$) — NH — (CH$_2$)$_2$ — phenyl — OH | 105–107 | −18 | <25 |
| 16 | t-Bu, HO, t-Bu phenyl — CH(PO$_3$Me$_2$) — NH — (CH$_2$)$_2$ — phenyl — Cl | 133–133.5 | −28 | 4.9 |
| 17 | t-Bu, HO, t-Bu phenyl — CH(PO$_3$Et$_2$) — NH — (CH$_2$)$_2$ — phenyl — Cl | 119.5–121 | −43 | 5.3 |
| 18 | t-Bu, HO, t-Bu phenyl — CH(PO$_3$Pr$_2$) — NH — (CH$_2$)$_2$ — phenyl — Cl | 116–118 | −23 | 2.9 |
| 19 | t-Bu, HO, t-Bu phenyl — CH(PO$_3$iPr$_2$) — NH — (CH$_2$)$_2$ — phenyl — Cl | 133–134 | −33 | 3.0 |
| 20 | t-Bu, HO, t-Bu phenyl — CH(PO$_3$Bu$_2$) — NH — (CH$_2$)$_2$ — phenyl — Cl | 65–67 | −9 | 3.4 |
| 21 | t-Bu, HO, t-Bu phenyl — CH(PO$_3$Me$_2$) — NH — (CH$_2$)$_3$ — phenyl | 78–79 | −33 | <25 |

TABLE 1-continued

Aminophosphonates substituted by phenol groups (I)

$$\underset{X^2}{\underset{X^3O}{\overset{X^1}{\bigcirc}}} (B)_n\underset{Z-N-A}{\overset{PO_3R_2}{\underset{|}{C}-H}} \quad (I)$$

| Compound | Structure | mp (°C.) | Plasma Cholesterol (% Control) | Antioxidant Activity IC$_{50}$ (μM) |
|---|---|---|---|---|
| 22 | 3,5-di-t-Bu-4-HO-C$_6$H$_2$-CH(PO$_3$Et$_2$)-NH-(CH$_2$)$_3$-C$_6$H$_5$ | 99–100 | −53 | 4.0 |
| 23 | 3,5-di-t-Bu-4-HO-C$_6$H$_2$-CH(PO$_3$Pr$_2$)-NH-(CH$_2$)$_3$-C$_6$H$_5$ | 91–92 | −4 | <25 |
| 24 | 3,5-di-t-Bu-4-HO-C$_6$H$_2$-CH(PO$_3^i$Pr$_2$)-NH-(CH$_2$)$_3$-C$_6$H$_5$ | 126–127 | −22 | <25 |
| 25 | 3,5-di-t-Bu-4-HO-C$_6$H$_2$-CH(PO$_3$Bu$_2$)-NH-(CH$_2$)$_3$-C$_6$H$_5$ | 57–60 | −4 | <25 |
| 26 | 3,5-di-t-Bu-4-HO-C$_6$H$_2$-CH(PO$_3$Et$_2$)-NH-(CH$_2$)$_3$-C$_6$H$_5$ · HCl | 132–134 | −11 | <25 |
| 27 | 3,5-di-t-Bu-4-HO-C$_6$H$_2$-CH(PO$_3$Et$_2$)-NH-(CH$_2$)$_4$-C$_6$H$_5$ | 93–94 | −43 | 2.1 |
| 28 | 3,5-di-t-Bu-4-HO-C$_6$H$_2$-CH(PO$_3$Et$_2$)-NH-(CH$_2$)$_2$-O-C$_6$H$_5$ | 75–77 | +4 | <25 |

TABLE 1-continued

Aminophosphonates substituted by phenol groups (I)

| Compound | Structure | mp (°C.) | Plasma Cholesterol (% Control) | Antioxidant Activity IC$_{50}$ (μM) |
|---|---|---|---|---|
| 29 | 3,5-di-t-Bu-4-HO-C$_6$H$_2$-CH(PO$_3$Et$_2$)-NH-CH(CH$_3$)-C$_6$H$_5$ | 95–110 | −32 | 5.5 |
| 30 | 3,5-di-t-Bu-4-HO-C$_6$H$_2$-CH(PO$_3$Et$_2$)-NH-CH(CH$_3$)-(CH$_2$)$_2$-C$_6$H$_5$ | 110–111 | −12 | 15.6 |
| 31 | 3,5-di-t-Bu-4-HO-C$_6$H$_2$-CH(PO$_3$Et$_2$)-NH-CH(CH$_3$)-naphthyl | 95–97 | −3 | <25 |
| 32 | 3,5-di-t-Bu-4-HO-C$_6$H$_2$-CH(PO$_3$Et$_2$)-NH-CH(C$_6$H$_5$)$_2$ | 156–160 | −12 | <25 |
| 33 | 3,5-di-t-Bu-4-HO-C$_6$H$_2$-CH(PO$_3$Et$_2$)-NH-CH(C$_6$H$_5$)-CH$_2$-C$_6$H$_5$ | 107.5–108.5 | −14 | <25 |
| 34 | 3,5-di-t-Bu-4-HO-C$_6$H$_2$-CH(PO$_3$Et$_2$)-NH-(CH$_2$)$_2$-N(piperidine) | wax | −5 | >10 |
| 35 | 3,5-di-t-Bu-4-HO-C$_6$H$_2$-CH(PO$_3$Et$_2$)-NH-CH(CH$_2$C(Me)$_2$NH)(CMe$_2$Me) | 135–137 | −17 | >25 |

TABLE 1-continued

Aminophosphonates substituted by phenol groups (I)

$$\text{Structure (I): } X^3O\text{-phenyl(with }X^1, X^2\text{)-}(B)_n\text{-C(PO}_3R_2\text{)(H)-N(Z)(A)}$$

| Compound | Structure | mp (°C.) | Plasma Cholesterol (% Control) | Antioxidant Activity IC$_{50}$ (μM) |
|---|---|---|---|---|
| 36 | 3,5-di-t-Bu-4-HO-C$_6$H$_2$-CH(PO$_3$Et$_2$)-NH-(4-piperidinyl)-N-CH$_2$-C$_6$H$_5$ | 120–123 | −6 | <25 |
| 37 | 3,5-di-t-Bu-4-HO-C$_6$H$_2$-CH(PO$_3$Et$_2$)-NH-(CH$_2$)$_2$-(N-methylpyrrol-2-yl) | 107–108 | +12 | 4.0 |
| 38 | 3,5-di-t-Bu-4-HO-C$_6$H$_2$-CH(PO$_3$Et$_2$)-NH-CH$_2$-(3,4-methylenedioxyphenyl) | 122.5–123.5 | −40 | 4.3 |
| 39 | 3,5-di-t-Bu-4-HO-C$_6$H$_2$-CH(PO$_3$Et$_2$)-NH-CH$_2$-(3,4-dimethoxyphenyl) | 125–130 | −4 | 4.9 |
| 40 | 3,5-di-t-Bu-4-HO-C$_6$H$_2$-CH(PO$_3$Et$_2$)-NH-CH$_2$-(3,5-di-t-Bu-4-HO-C$_6$H$_2$) | 120–123 | −25 | |
| 41 | 3,5-di-t-Bu-4-HO-C$_6$H$_2$-CH(PO$_3$Et$_2$)-NH-(pyridin-3-yl) | 155–156 | −35 | 3.5 |

TABLE 1-continued

Aminophosphonates substituted by phenol groups (I)

$$\text{X}^3\text{O}-\underset{\underset{\text{X}^2}{|}}{\overset{\overset{\text{X}^1}{|}}{\text{C}_6\text{H}_2}}-(\text{B})_n-\underset{\underset{\text{Z}-\text{N}-\text{A}}{|}}{\overset{\overset{\text{PO}_3\text{R}_2}{|}}{\text{C}}}-\text{H} \quad \text{(I)}$$

| Compound | Structure | mp (°C.) | Plasma Cholesterol (% Control) | Antioxidant Activity IC$_{50}$ (μM) |
|---|---|---|---|---|
| 42 | 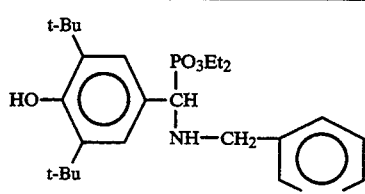 | 100–101 | −43 | 12.8 |
| 43 | 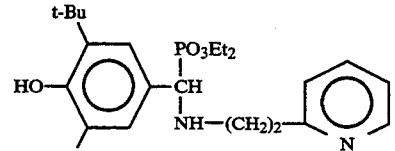 | 76–78 | −35 | <25 |
| 44 | 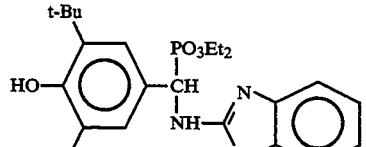 | 198–199 | −17 | <25 |
| 45 | 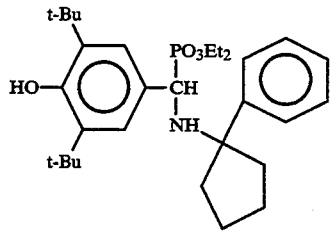 | 114–115 | −14 | <25 |
| 46 | 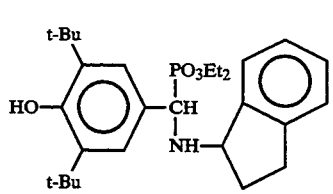 | 161–163 | −8 | 3.8 |
| 47 | 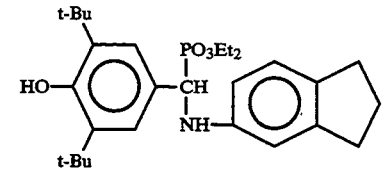 | 130–132 | −2 | 2.7 |

TABLE 1-continued

Aminophosphonates substituted by phenol groups (I)

$$\text{structure (I): } X^3O\text{-phenyl(with }X^1, X^2\text{)-(B)}_n\text{-C(PO}_3R_2)(H)(Z\text{-N-A)}$$

| Compound | Structure | mp (°C.) | Plasma Cholesterol (% Control) | Antioxidant Activity IC$_{50}$ (μM) |
|---|---|---|---|---|
| 48 | 3,5-di-t-Bu-4-HO-phenyl-CH(PO$_3$Et$_2$)-NH-fluoren-2-yl | 153-155 | +3 | <25 |
| 49 | 3,5-di-t-Bu-4-HO-phenyl-CH(PO$_3$Et$_2$)-N(CH$_3$)-CH$_2$-(pyridin-3-yl) | | −19 | 12.8 |
| 50 | 3,5-di-t-Bu-4-HO-phenyl-CH(PO$_3$Et$_2$)-N(CH$_3$)-phenyl | | +5 | 2.9 |
| 51 | 3,5-di-t-Bu-4-HO-phenyl-CH(PO$_3$Et$_2$)-N(CO-CH$_3$)-CH$_2$-phenyl | | | <25 |
| 52 | 3,5-di-t-Bu-4-HO-phenyl-CH(PO$_3$Et$_2$)-N(CO-CF$_3$)-CH$_2$-phenyl | 109-133 | | <25 |
| 53 | 3,5-di-t-Bu-4-HO-phenyl-CH(PO$_3$Et$_2$)-N(CO-CH$_3$)-(CH$_2$)$_2$-phenyl | | | <25 |
| 54 | 3,5-di-t-Bu-4-HO-phenyl-CH(PO$_3$Et$_2$)-N(CO-CF$_3$)-(CH$_2$)$_2$-phenyl | | | <25 |

TABLE 1-continued

Aminophosphonates substituted by phenol groups (I)

$$\text{X}^3\text{O} - \underset{\underset{\text{X}^2}{|}}{\overset{\overset{\text{X}^1}{|}}{\text{C}_6\text{H}_2}} - (\text{B})_n - \underset{\underset{\text{Z}-\text{N}-\text{A}}{|}}{\overset{\overset{\text{PO}_3\text{R}_2}{|}}{\text{C}}} - \text{H} \quad \text{(I)}$$

| Compound | Structure | mp (°C.) | Plasma Cholesterol (% Control) | Antioxidant Activity IC$_{50}$ (μM) |
|---|---|---|---|---|
| 55 | t-Bu, HO, t-Bu phenyl; CH(PO$_3$Bu$_2$)-N(COCF$_3$)-(CH$_2$)$_2$-C$_6$H$_4$-Cl | 83–87 | | >25 |
| 56 | t-Bu, HO, t-Bu phenyl; CH(PO$_3$Et$_2$)-N(COCF$_3$)-CH(CH$_2$-Ph)-Ph | 129–131 | | <25 |
| 57 | t-Bu, HO, t-Bu phenyl; CH(PO$_3$Et$_2$)-N(COCF$_3$)-(CH$_2$)$_2$-O-Ph | | | <25 |
| 58 | t-Bu, HO, t-Bu phenyl; CH(PO$_3$Et$_2$)-N(COCF$_3$)-C$_6$H$_4$-C$_5$H$_{11}$ | 88–92 | | <25 |
| 59 | t-Bu, HO, t-Bu phenyl; CH(PO$_3$Me$_2$)-N(COCH$_3$)-(CH$_2$)$_3$-Ph | 68–70 | −36 | <25 |
| 60 | t-Bu, HO, t-Bu phenyl; CH(PO$_3$Et$_2$)-N(COCH$_3$)-(CH$_2$)$_3$-Ph | 135–136 | −49 | 2.6 |
| 61 | t-Bu, HO, t-Bu phenyl; CH(PO$_3$Pr$_2$)-N(COCH$_3$)-(CH$_2$)$_3$-Ph | 107–108 | −43 | <25 |

TABLE 1-continued

Aminophosphonates substituted by phenol groups (I)

$$\text{structure (I): } X^3O\text{-phenyl with } X^1, X^2 \text{ substituents, } -(B)_n-\underset{Z-N-A}{\overset{PO_3R_2}{\underset{|}{C}}}-H$$

| Compound | Structure | mp (°C.) | Plasma Cholesterol (% Control) | Antioxidant Activity IC$_{50}$ (μM) |
|---|---|---|---|---|
| 62 | HO-[3,5-di-t-Bu-phenyl]-CH(PO$_3$iPr$_2$)-N(COCH$_3$)-(CH$_2$)$_3$-phenyl | 123–124 | −32 | <25 |
| 63 | HO-[3,5-di-t-Bu-phenyl]-CH(PO$_3$Bu$_2$)-N(COCH$_3$)-(CH$_2$)$_3$-phenyl | 65–67 | +4 | <25 |
| 64 | HO-[3,5-di-t-Bu-phenyl]-CH(PO$_3$Et$_2$)-N(COCF$_3$)-(CH$_2$)$_3$-phenyl | 74–79 | | <25 |
| 65 | HO-[3,5-di-t-Bu-phenyl]-CH(PO$_3$Et$_2$)-NH-cyclohexyl | 108–115 | +7 | <25 |
| 66 | HO-[3,5-di-t-Bu-phenyl]-CH(PO$_3$Et$_2$)-N(COCF$_3$)-(CH$_2$)$_4$-phenyl | | | <25 |
| 67 | CH$_3$O-[3,5-di-t-Bu-phenyl]-CH(PO$_3$Et$_2$)-NH-(CH$_2$)$_3$-phenyl | | −22 | >25 |
| 68 | HO-[3,5-di-t-Bu-phenyl]-CH$_2$-CH(PO$_3$Et$_2$)-NH-(CH$_2$)$_3$-phenyl | | −18 | <25 |

TABLE 1-continued

Aminophosphonates substituted by phenol groups (I)

$$\text{(I)}$$

Structure with $X^1$, $X^2$, $X^3O$ on phenyl ring, $(B)_n-C(H)(PO_3R_2)-N(Z)-A$

| Compound | Structure | mp (°C.) | Plasma Cholesterol (% Control) | Antioxidant Activity IC$_{50}$ (μM) |
|---|---|---|---|---|
| 69 | $C_4H_9O$-C$_6H_4$-CH(PO$_3$Et$_2$)-NH-(CH$_2$)$_2$-C$_6H_5$ | wax | +2 | >10 |
| 70 | HO, CH$_3$O-C$_6H_3$-CH(PO$_3$Et$_2$)-NH-CH$_2$-C$_6H_5$ | | −10 | >25 |
| 71 | CH$_3$O, HO, CH$_3$O-C$_6H_2$-CH(PO$_3$Et$_2$)-NH-CH$_2$-C$_6H_5$ | | +1 | >25 |
| 72 | CH$_3$, HO, CH$_3$-C$_6H_2$-CH(PO$_3$Et$_2$)-NH-(CH$_2$)$_2$-C$_6H_5$ | | −1 | >25 |
| 73 | s-Bu, HO, s-Bu-C$_6H_2$-CH(PO$_3$Et$_2$)-NH-(CH$_2$)$_2$-C$_6H_5$ | | −40 | 2.9 |
| 74 | $^i$Pr, HO, $^i$Pr-C$_6H_2$-CH(PO$_3$Et$_2$)-NH-(CH$_2$)$_2$-C$_6H_5$ | 78–82 | −16 | 4.4 |
| 75 | t-Bu, HO, CH$_3$-C$_6H_2$-CH(PO$_3$Et$_2$)-NH-(CH$_2$)$_2$-C$_6H_5$ | | −12 | 4.8 |

TABLE 1-continued

Aminophosphonates substituted by phenol groups (I)

$$\text{Structure: } X^3O\text{-phenyl}(X^1,X^2)\text{-}(B)_n\text{-C}(PO_3R_2)(H)\text{-N}(Z)\text{-A} \quad (I)$$

| Compound | Structure | mp (°C.) | Plasma Cholesterol (% Control) | Antioxidant Activity IC$_{50}$ (μM) |
|---|---|---|---|---|
| 76 | HO–C$_6$H$_4$–CH(PO$_3$Et$_2$)–NH–(CH$_2$)$_2$–C$_6$H$_4$–Cl | 87–88 | −16 | >25 |
| 77 | HO,O$_2$N–C$_6$H$_3$–CH(PO$_3$Et$_2$)–NH–(CH$_2$)$_3$–C$_6$H$_5$ | 64–65 | −3 | >25 |
| 78 | HO,HO–C$_6$H$_3$–CH(PO$_3$Et$_2$)–NH–(CH$_2$)$_3$–C$_6$H$_5$ | wax | −5 | <25 |
| 79 | CH$_3$O–C$_6$H$_4$–CH(PO$_3$Et$_2$)–NH–(CH$_2$)$_3$–C$_6$H$_5$ | | +9 | >25 |
| 80 | methylenedioxyphenyl–CH(PO$_3$Et$_2$)–NH–(CH$_2$)$_3$–C$_6$H$_5$ | | −29 | >25 |
| 81 | 3,5-di-t-Bu-4-HO–C$_6$H$_2$–CH(PO$_3$H$_2$)–NH–(CH$_2$)$_3$–C$_6$H$_5$ | 162–169 | | |
| 82 | 3,5-di-t-Bu-4-HO–C$_6$H$_2$–CH(PO$_3$tBu$_2$)–NH–(CH$_2$)$_2$–C$_6$H$_4$–Cl | 152.5–153.5 | | |
| 83 | 3,5-di-t-Bu-4-HO–C$_6$H$_2$–CH(PO$_3$Et$_2$)–NH$_2$ | 129–130 | +4 | |

TABLE 1-continued

Aminophosphonates substituted by phenol groups (I)

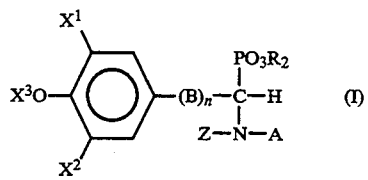

| Compound | Structure | mp (°C.) | Plasma Cholesterol (% Control) | Antioxidant Activity IC$_{50}$ (μM) |
|---|---|---|---|---|
| 84 | t-Bu, HO, t-Bu — PO$_3$Et$_2$ / CH / NH—CH$_2$—CH=CH$_2$ | 91–92 | −19 | |
| 85 | t-Bu, HO, t-Bu — PO$_3$Et$_2$ / CH / NH—COO—CH$_2$—Ph | 193–194 | 0 | |
| 86 | t-Bu, HO, t-Bu — PO$_3$Et$_2$ / CH / NH—CH$_2$-pyridyl | 87–91 | −15 | |
| 87 | HO—Ph—CH(PO$_3$Et$_2$)—NH—CH$_2$—(3,5-di-t-Bu-4-OH-phenyl) | 202.5–203.5 | | |
| 88 | t-Bu, HO, t-Bu — PO$_3$Et$_2$ / CH / NH—CH$_2$—CH(CH$_3$)—Ph | | | |
| 89 | t-Bu, HO, t-Bu — PO$_3$Et$_2$ / CH / NH—CH$_2$-pyridyl | 90–91 | | |
| 90 | t-Bu, HO, t-Bu —CH=CH—CH(PO$_3$Et$_2$)—NH—(CH$_2$)$_3$—Ph | | | |

TABLE 1-continued

Aminophosphonates substituted by phenol groups (I)

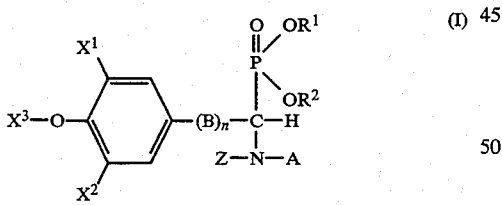

| Compound | Structure | mp (°C.) | Plasma Cholesterol (% Control) | Antioxidant Activity IC$_{50}$ (μM) |
|---|---|---|---|---|
| 91 | t-Bu, HO–, t-Bu, PO$_3$Et$_2$, CH, NH, (acetonide-phenyl side chain) | | −18 | |
| 92 | t-Bu, HO–, t-Bu, PO$_3$Et$_2$, CH, N–(CH$_2$)$_2$-pyridyl, CH$_3$—CO | | | |
| 93 | t-Bu, HO–, t-Bu, PO$_3$Et$_2$, CH, N–(CH$_2$)$_3$-phenyl, C$_3$F$_7$—CO | | 93–97 | |

We claim:

1. Aminophosphonate derivatives alpha-substituted by phenol groups, of formula (I)

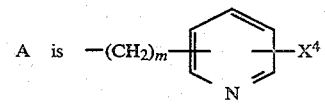

where:

X$^1$, X$^2$, identical or different, are H, a straight or branched alkyl or alkoxy group having from 1 to 8 carbon atoms, a hydroxy group or a nitro group, X$^3$ is H, an alkyl group from 1 to 4 carbon atoms, X$^3$O and one of the two other substituents X$^1$ or X$^2$ may form an alkylidene dioxy ring having from 1 to 4 carbon atoms, R$^1$, R$^2$ identical or different, are H, a straight or branched alkyl group having from 1 to 6 carbon atoms, B is CH$_2$, CH$_2$—CH$_2$ or CH=CH, n is zero or 1, Z is H, a straight or branched alkyl group having from 1 to 8 carbon atoms, an acyl group R$^3$—CO where R$^3$ is an alkyl group from 1 to 4 carbon atoms, a perfluoroalkyl group from 1 to 4 carbon atoms, A is —(CH$_2$)$_m$—pyridyl—X$^4$ where:

m is an integer from 0 to 5, X$^4$ is H, a straight or branched alkyl or alkoxy group from 1 to 8 carbon atoms, a hydroxy, trifluoromethyl, nitro, amino, dimethylamino, diethyl amino group, a halogen atom (F, Cl, Br, I).

2. Compounds of formula (I) according to claim 1, wherein
X$^1$ and X$^2$ are each a tert-butyl group,
X$^3$ is H,
R$^1$ and R$^2$ are each an ethyl group,
n is zero, and
Z is H.

3. Aminophosphonate derivatives according to claim 1, selected among the group comprising:
diethyl α-(3,5-di-tert-butyl-4-hydroxyphenyl)-N-(3-picolyl)-aminomethylphosphonate, diethyl α-(3,5-di-tert-butyl-4-hydroxyphenyl)-N-[2-(2-pyridyl)ethyl]-aminomethylphosphonate,
diethyl α-(3,5-di-tert-butyl-4-hydroxyphenyl)-N-(3-pyridyl)-aminomethylphosphonate,
diethyl α-(3,5-di-tert-butyl-4-hydroxyphenyl)-N-methyl-N-(3-picolyl)-aminomethylphosphonate,
diethyl α-(3,5-di-tert-butyl-4-hydroxyphenyl) -N-(4-picolyl)-aminomethylphosphonate,
diethyl α-(3,5-di-tert-butyl-4-hydroxyphenyl)-N-acetyl-N-[2-(2-pyridyl)ethyl]-aminomethylphosphonate,
diethyl α-(3,5-di-tert-butyl-4-hydroxyphenyl)-N-(2-picolyl)-aminomethylphosphonate.

4. A pharmaceutical composition comprising an effective amount of aminophosphonate of formula (I) according to claim 1 in the amount effective for decreasing plasma cholesterol and blood peroxides, in combination with a pharmaceutically acceptable carrier.

5. A pharmaceutical composition comprising an effective amount of aminophosphonate of formula (I) according to claim 3 in the amount effective for decreasing plasma cholesterol and blood peroxides, in combination with a pharmaceutically acceptable carrier.

* * * * *